United States Patent [19]

Martinez

[11] 4,305,395

[45] Dec. 15, 1981

[54] METHOD OF POSITIONING TUBING IN LACRIMAL DUCTS AND INTUBATION SET THEREFOR

[75] Inventor: Miguel Martinez, Clearwater, Fla.

[73] Assignee: Concept, Inc., Clearwater, Fla.

[21] Appl. No.: 62,157

[22] Filed: Jul. 30, 1979

[51] Int. Cl.³ .......................................... A61M 25/00
[52] U.S. Cl. ................................ 128/348; 128/350 R; 3/1
[58] Field of Search ................ 128/1 R, 348, 350 R, 128/349 R; 3/1

[56] References Cited

U.S. PATENT DOCUMENTS

| | | | |
|---|---|---|---|
| 2,154,968 | 4/1939 | Alkio | 128/348 |
| 2,393,003 | 1/1946 | Smith | 128/349 R |
| 3,225,762 | 12/1965 | Guttman | 128/348 X |
| 3,695,921 | 10/1972 | Shepherd et al. | 128/348 X |
| 3,726,284 | 4/1973 | Parker | 128/350 R |
| 3,908,664 | 9/1975 | Loseff | 128/350 R |
| 3,948,272 | 4/1976 | Guibor | 128/350 R |

*Primary Examiner*—Frank A. Spear, Jr.
*Attorney, Agent, or Firm*—Robert H. Epstein

[57] ABSTRACT

An intubation set includes a flexible sheath, a probe inserted in the flexible sheath having a proximal end extending out of the sheath and a length of tubing secured to the sheath to permit the tubing to be positioned in a body by inserting the probe within the sheath into the body, withdrawing the probe from the sheath and pulling the sheath through the body to position the tubing by grasping an end of the sheath. A method of positioning the length of tubing in the lacrimal ducts utilizes the intubation set with a pair of flexible sheaths connected with the tubing and a pair of probes received in the sheaths.

10 Claims, 6 Drawing Figures

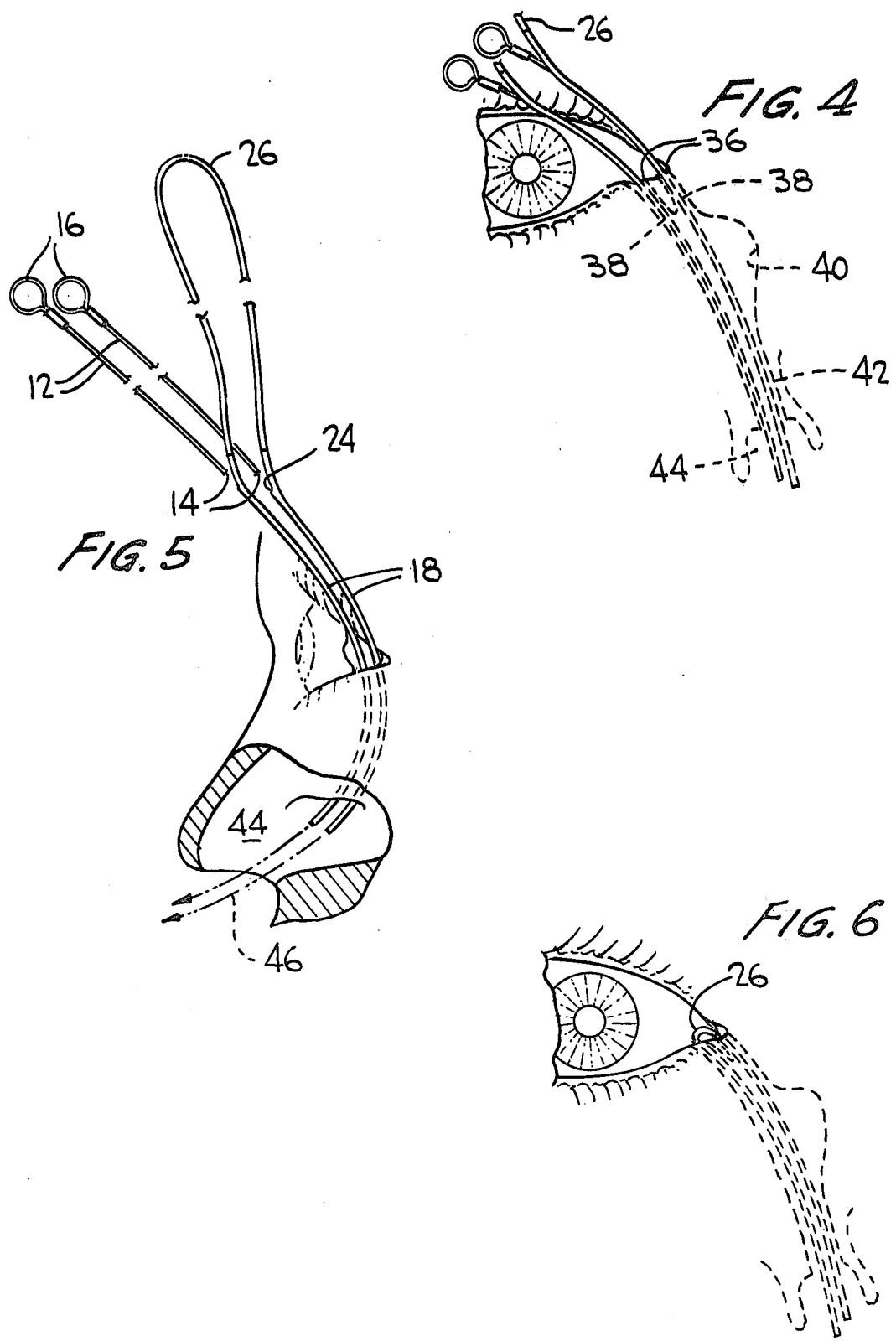

METHOD OF POSITIONING TUBING IN LACRIMAL DUCTS AND INTUBATION SET THEREFOR

BACKGROUND OF THE INVENTION

1. Field of the Invention

The present invention pertains to intubation sets and methods for positioning an elongate member in a body passage and, more particularly, to an intubation set for positioning a length of tubing in the lacrimal ducts.

2. Discussion of the Prior Art

The insertion of an elongate member in a passage within the body is a frequently required surgical procedure; however, prior art intubation sets have, in the past, required the passing of a metal probe through the passage to position the elongate member and, thus, have had the disadvantages of creating a traumatic situation when the probe is finally withdrawn from the body and requiring extreme care to be taken in manipulation of the probe and in selecting a suitable material for the probe.

The insertion of an elongate member in the lacrimal ducts is a frequent surgical procedure for reconstruction or other remedial purposes for the reasons to follow. Lacrimal fluid or tears are continuously supplied from the lacrimal gland to wash across the sclera and other conjunctival components and the cornea. The excess lacrimal fluid is drained through a network of passages commencing with the puncta which appear as a small papilla adjacent the inner canthus or inner corner of the eye, the lacrimal fluid being collected in the lacrimal sac by a number of canaliculi connecting the puncta with the lacrimal sac. The lacrimal sac is drained through the nasolacrimal duct which passes into the inferior nasal meatus. This network of passages is referred to hereinafter as the lacrimal ducts. Frequently permanent closures occur in the canaliculi, the lacrimal sac, or the nasolacrimal duct and the lacrimal fluid can no longer be drained therethrough. Upon occurrence of a closure in the lacrimal ducts, the eye will fill with tears, and stagnating tears, as well as being uncomfortable, can result in infection and inflammatory irritation of the mucous membrane with proliferation of the epithelium, hyperemia, and a purulent exudation into the conjunctiva.

U.S. Pat. No. 2,154,968 to Alkio discloses a method of enlarging and draining the lacrimal ducts using a tube for preliminary enlargement and then inserting a spiral cannula into the ducts through the nose and behind the tube. The tube and the cannula are drawn upwardly in the duct, and the tube is removed with the cannula remaining in the duct for drainage of secretions between the spirals of the cannula.

U.S. Pat. No. 3,726,284 to Parker discloses a replacement tube for the lacrimal drainage ducts which tube includes a pair of elongated end portions and an expanded central portion having a drainage passage adjoining adjacent ends of the end portions. Each of the end portions has a drain passage communicating with the expanded portion.

U.S. Pat. No. 3,948,272 to Guibor discloses a reconstruction device for lacrimal drainage ducts including a pair of metal probes connected with a length of tubing, the metal probes being inserted through the lacrimal ducts and withdrawn through the nose to position the tubing in the lacrimal ducts. While the Guibor device has been widely accepted, the fact that the metal probe must be passed entirely through the lacrimal ducts has the drawback, as mentioned above, of increasing trauma for the patient.

SUMMARY OF THE INVENTION

Accordingly, it is a primary object of the present invention to overcome the above-mentioned disadvantages of the prior art by providing an intubation set useful for positioning an elongate member in a body passage without requiring the complete passage of a probe therethrough and by providing a method therefor.

Another object of the present invention is to utilize a flexible tube as a sheath for a probe for insertion in the lacrimal ducts with the probe being removable from the sheath to permit an elongate member secured to the sheath to be positioned in the lacrimal ducts by pulling the sheath through the nose.

A further object of the present invention is to connect a length of tubing with a pair of flexible tubular sheaths having probes slidably received therein to permit the probes to be inserted in the lacrimal ducts and withdrawn from the sheaths such that the sheaths can be pulled through the lacrimal ducts to position the length of tubing therein.

Yet another object of the present invention is to position a length of tubing in the lacrimal ducts by passing a pair of probes, each inserted in a flexible, tubular sheath connected with the length of tubing, through the lacrimal ducts and into the nose, withdrawing the probes from the tubular sheaths and grasping the ends of the tubular sheaths through the nose and pulling the tubular sheaths therethrough to position the length of tubing in the lacrimal ducts.

SUMMARY OF THE INVENTION

Accordingly, it is a primary object of the present invention to overcome the above-mentioned disadvantages of the prior art by providing an intubation set useful for positioning an elongate member in a body passage without requiring the complete passage of a probe therethrough and by providing a method therefor.

Another object of the present invention is to utilize a flexible tube as a sheath for a probe for insertion in the lacrimal ducts with the probe being removable from the sheath to permit an elongate member secured to the sheath to be positioned in the lacrimal ducts by pulling the sheath through the nose.

A further object of the present invention is to connect a length of tubing with a pair of flexible tubular sheaths having probes slidably received therein to permit the probes to be inserted in the lacrimal ducts and withdrawn from the sheaths such that the sheaths can be pulled through the lacrimal ducts to position the length of tubing therein.

Yet another object of the present invention is to position a length of tubing in the lacrimal ducts by passing a pair of probes, each inserted in a flexible, tubular sheath connected with the length of tubing, through the lacrimal ducts and into the nose, withdrawing the probes from the tubular sheaths and grasping the ends of the tubular sheaths through the nose and pulling the tubular sheaths therethrough to position the length of tubing in the lacrimal ducts.

Some of the advantages of the present invention over the prior art are that the intubation set is simple in construction and inexpensive to manufacture and the method of use thereof permits positioning of an elongate member in a body passage without requiring the complete passage of a metal probe therethrough thereby obviating the trauma associated with drawing a metal probe through the body and permitting a wider choice of materials for the probe.

The present invention is generally characterized in an intubation set including a flexible tubular sheath having a distal end and a proximal end, a probe for insertion in the sheath with a distal end disposed adjacent the distal end of the sheath and a proximal end extending out of the sheath to permit the probe to be withdrawn from the sheath, and an elongate member secured to the sheath at the proximal end thereof whereby the elongate member can be positioned in a body passage by inserting the probe within the sheath into the passage, withdrawing the probe from the sheath and pulling the sheath through the body to position the elongate member by grasping the distal end of the sheath.

The present invention is further generally characterized in an intubation set for use in reconstruction of the lacrimal ducts including tubing means having a pair of flexible sheath portions each having a closed end and a side wall with an opening therein and a tubing portion connecting the sheath portions, and a pair of probes each slidably received in one of the sheath portions and having a distal end disposed at the closed end thereof and a proximal end extending through the opening whereby the tubing portion can be positioned in the lacrimal ducts by inserting the probes carrying the sheath portions into the lacrimal drainage ducts, withdrawing the probes from the sheath portions and pulling the sheath portions through the lacrimal ducts by grasping the closed ends.

The present invention is still further generally characterized in a method of positioning a length of tubing in the lacrimal ducts including the steps of passing a pair of probes through the puncti lacrimalia, the lacrimal ducts, the lacrimal sacs, the nasolacrimal ducts and into the nose, the probes each being inserted in a flexible tubular sheath and the tubular sheaths being connected with the length of tubing, withdrawing the probes from the tubular sheaths, grasping the ends of the tubular sheaths through the nose, pulling the tubular sheaths through the nose to position the length of tubing in the lacrimal ducts, and separating the length of tubing from the tubular sheaths.

Other objects and advantages of the present invention will become apparent from the following description of the preferred embodiment taken in conjunction with the accompanying drawings.

BRIEF DESCRIPTION OF THE DRAWINGS

FIGS. 4, 5 and 6 illustrate the method of utilizing the intubation set of FIG. 1 to insert a length of tubing in the lacrimal ducts in accordance with the present invention.

DESCRIPTION OF THE PREFERRED EMBODIMENT

Figure 1:
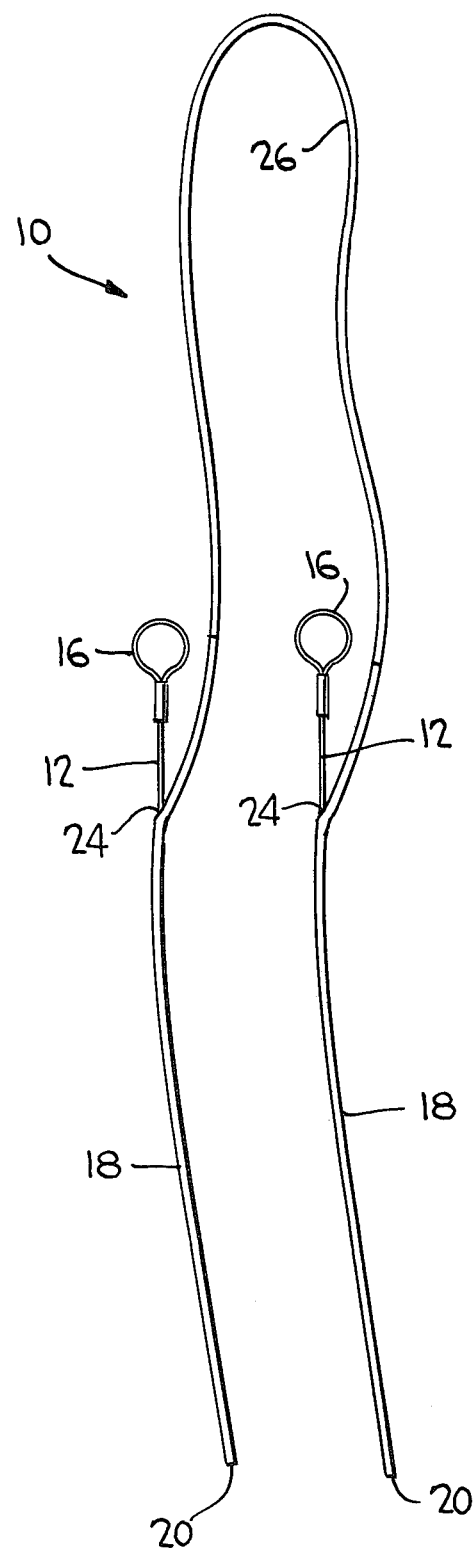
FIG. 1 is a perspective view of an intubation set according to the present invention.

An intubation set 10 according to the present invention is shown in FIG. 1 and includes a pair of probes 12 of identical construction, each probe having a wire-like configuration with a distal end 14 and a finger-grip loop 16 disposed at a proximal end. The probes can be made of any suitable relatively stiff material, such as stainless steel, since, as will be explained in more detail hereinafter, the probes do not come into contact with the body and are not required to be extremely flexible as the probes do not have to be bent in use either for insertion or removal.

Figure 3:
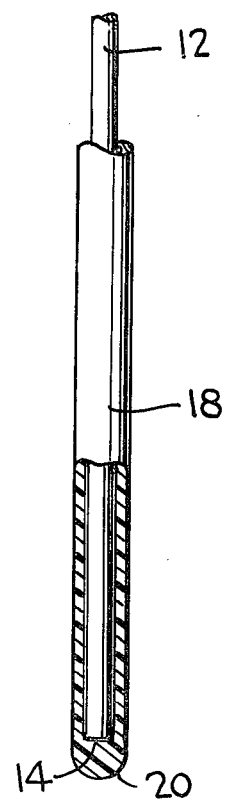
FIG. 3 is a partial section of the distal ends of the probes and flexible tubular sheaths of the intubation set of FIG. 1.

The probes 12 are each slidably inserted in a flexible tubular sheath 18 having a closed distal end 20 with a globular, curved configuration, as best shown in FIG. 3, an open proximal end 22 and an opening 24 in the side wall adjacent but longitudinally spaced from the proximal end 22. The tubular sheaths 18 can be made of any suitable flexible material of sufficient strength to prevent tearing by the probes while being acceptable for passage through the human body, an example of such materials being a polyamide or nylon, such as Supramid imported into the United States by Dr. S. Jackson of Washington, D.C. The distal end 20 can be closed when the sheath is made of polyamide by heating the end to form the globular tip.

Figure 2:
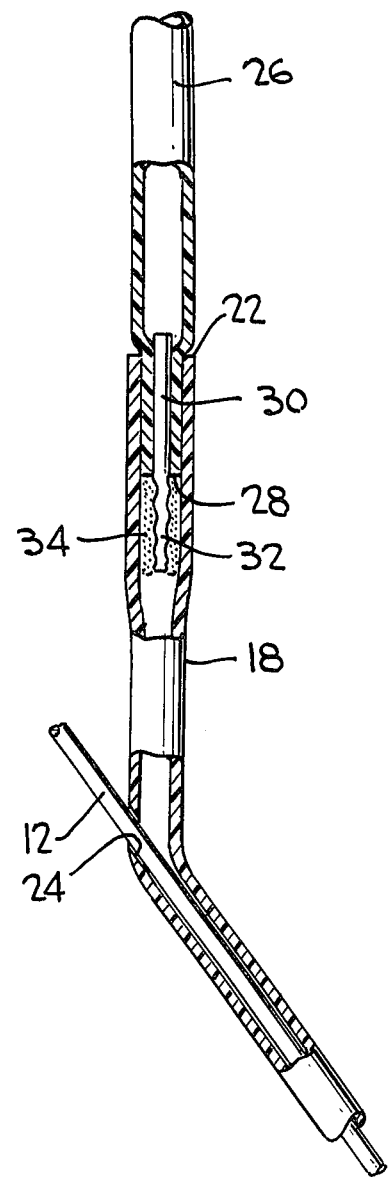
FIG. 2 is a partial view of the connection of the flexible, tubular sheaths with the length of tubing, with parts broken away, of the intubation set of FIG. 1.

An elongate member in the form of a length of tubing 26 is connected at opposite ends 28 with the proximal ends 22 of the tubular sheaths 18 by means of rod-like connectors 30 formed of filaments of plastic material, such as a polyamide, like Supramid, as shown in FIG. 2. The connectors 30 have irregular surface portions 32 formed, for example, by mechanically disfiguring the filaments, and the connectors are coaxially aligned within the ends 28 of the tubing 26 and the proximal ends 22 of the tubular sheaths with the ends 28 of the tubing receiving the smooth surface portions of the connectors with a friction fit while the irregular surface portions 32 are bonded in the ends 22 of the tubular sheaths by an epoxy 34. The ends 28 of the tubing are received in the ends 22 of the tubular sheaths with a friction fit. The tubing 26 is made of a material acceptable for retention in the body, preferably a silicone rubber, such as Silastic manufactured by Dow Corning. The elongate member 26 will be discussed hereinafter as being a hollow tubing; however, the elongate member can have any desired cross sectional configuration, either hollow or solid.

While the intubation set 10 can be used to position an elongate member within any passage in the body, the intubation set is particularly advantageous for use in positioning a length of tubing in the lacrimal ducts, and a method of positioning the tubing 26 in accordance with the present invention is described hereinafter with reference to FIGS. 4, 5 and 6.

The intubation set 10 will normally be packaged in a sterilized condition with the probes 12 inserted in the sheaths 18; and, in use, the intubation set is removed from the package and the distal ends of the probes within the sheaths are inserted in the puncti lacrimalia 36. The probes within the sheaths are, thus, passed through the canaliculi 38, the lacrimal sac 40 and the nasolacrimal ducts 42 into the nose 44, as shown in FIG. 4. Accordingly, the distal ends of sheaths 18 extend into the nose; and, with the intubation set so positioned, the probes 12 are slidably withdrawn from the sheaths 18, as shown in FIG. 5, such that the distal ends of the sheaths can be grasped to pull the sheaths through the nose, as indicated by arrows 46, with minimal trauma due to the flexible nature of the sheaths. As the sheaths are pulled through the nose, the tubing 26 is pulled into the lacrimal ducts, as shown in FIG. 6; and, with the tubing so positioned, the sheaths are severed from the tubing to permit the ends of the tubing to be secured in place, such as by knotting, taping or suturing.

The method of positioning the length of tubing in the lacrimal ducts, as described above, in accordance with the present invention has the advantages over the prior art in that the material from which the probes are made is not critical since the probes do not contact the body and do not have to be bent in use and trauma to the patient is minimized since the probes are not required to be drawn through the nose. Silicone rubber has been found to be the most desirable material for insertion and retention in the lacrimal ducts; however, silicone rubber is too soft and easily torn to permit its use in the sheaths. Accordingly, the sheaths are formed separately from the tubing and made of a more acceptable material, polyamide preferably; however, the sheaths and the length of tubing could be formed from a single tube of a material suitable for retention in the body for receiving the probes.

If desired, the intubation set 10 can be used to place a single sheath 18 in the lacrimal ducts to simplify the process of enlarging the lacrimal ducts. To this end, in accordance with the present invention, a probe 12 can be inserted in the open proximal end 22 of the sheath, and the probe within the sheath can be inserted in the lacrimal duct until the distal end reaches the nose when the probe is removed with the sheath remaining in place.

Inasmuch as the present invention is subject to many variations, modifications and changes in detail, it is intended that all subject matter discussed above or shown in the accompanying drawings be interpreted as illustrative and not in a limiting sense.

What is claimed is:

1. An intubation set for use in reconstruction of the lacrimal ducts comprising
    tubing means including a pair of flexible sheath portions each having a closed end and a side wall with an opening therein and a tubing portion connecting said sheath portions; and
    a pair of probes each slidably received in one of said sheath portions and having a distal end disposed at said closed end thereof and a proximal end extending through said opening whereby said tubing portion can be positioned in the lacrimal ducts by inserting said probes within said sheath portions into the lacrimal drainage ducts, withdrawing said probes from said sheath portions and pulling said sheath portions through the lacrimal ducts by grasping said closed end.

2. An intubation set as recited in claim 1 wherein said sheath portions are separate flexible tubular sheaths and said tubing portion is a separate length of tubing, said sheaths having open ends secured to opposite ends of said length of tubing.

3. An intubation set as recited in claim 2 wherein said opposite ends of said length of tubing are received in said open ends of said sheaths and further comprising a pair of rod-like connectors each extending coaxially through one of said open ends of said sheaths into one end of said length of tubing.

4. An intubation set as recited in claim 3 wherein said connectors have irregular surface portions bonded to said sheaths with an epoxy and smooth surface portions receiving said ends of said tubing with a friction fit.

5. An intubation set as recited in claim 4 wherein said length of tubing is made of silicone and said sheaths are made of polyamide.

6. An intubation set as recited in claim 5 wherein said probes are made of metal and have loops formed on said distal ends to facilitate handling.

7. An intubation set as recited in claim 2 wherein said length of tubing is made of silicone and said sheaths are made of polyamide.

8. An intubation set as recited in claim 1 wherein said sheath portions and said tubing portion of said tubing means are formed from a single tube of material.

9. A method of positioning a flexible elongate member in the lacrimal ducts comprising the steps of
    passing a pair of probes through the puncti lacrimalia, the canaliculi, the lacrimal sac, the nasolacrimal ducts and into the nose, the probes each being inserted in a flexible tubular sheath and the tubular sheaths being connected with the elongate member;
    withdrawing the probes from the tubular sheaths;
    grasping the ends of the tubular sheaths through the nose;
    pulling the tubular sheaths through the nose to position the elongate member in the lacrimal ducts; and
    separating the elongate member from the tubular sheaths.

10. The method as recited in claim 9 wherein the elongate member is a length of silicone tubing and the tubular sheaths are made of polyamide.

* * * * *